United States Patent [19]

Poletto et al.

[11] 4,120,891

[45] Oct. 17, 1978

[54] UREYLENE NAPHTHALENE SULFONIC ACIDS

[75] Inventors: John Frank Poletto, Nanuet; Seymour Bernstein, New City, both of N.Y.

[73] Assignee: American Cyanamid Company, Stamford, Conn.

[21] Appl. No.: 812,192

[22] Filed: Jul. 1, 1977

[51] Int. Cl.$^2$ .................. C07C 143/30; A61K 31/185
[52] U.S. Cl. .................................... 260/506; 424/315; 260/507 R
[58] Field of Search ........................ 260/506, 507 R

[56] References Cited

U.S. PATENT DOCUMENTS

| | | | |
|---|---|---|---|
| 4,046,805 | 9/1977 | Bernstein et al. | 260/506 |
| 4,051,176 | 9/1977 | Bernstein et al. | 260/506 |

*Primary Examiner*—Nicky Chan
*Attorney, Agent, or Firm*—Claude J. Caroli

[57] ABSTRACT

Ureylenebis-symmetrical-phenenylbiscarbonylimino-substituted phenylenecarbonylimino-tetranaphthalenepolysulfonic acid benzoic acid salts, and nitro- and amino-substituted phenylenebiscarbonylimino-substituted benzamido-phenylenedicarbonyl-dinaphthalenepolysulfonic acid benzoic acid salts which are intermediates for the preparation of the active ureides which have complement inhibiting activity.

6 Claims, No Drawings

UREYLENE NAPHTHALENE SULFONIC ACIDS

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–66; J. Allergy Clin. Immunol., 53, 298–302 (1974); Cold Spring Harbor Conf. Cell Proliferation 2/Proteases Biol. Control/229–241 (1975); Annals of Internal Medicine, 84, 580–593 (1976); "Complement: Mechanisms and Functions", Prentice-Hall, Englewood Cliffs, N.J. (1976).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) and attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327–339 (1952). The compound 8-(3-benzamido-4-methylbenzamido)naphthalene-1,3,5-trisulfonic acid (Suramin) is described as a competitive inhibitor of the complement system, Clin. Exp. Immunol., 10, 127–138 (1972). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 93, 629–640 (1964); The Journal of Immunology, 104, 279–288 (1970); The Journal of Immunology, 106, 241–245 (1971); and The Journal of Immunology, 111, 1061–1066 (1973).

It has been reported that the known complement inhibitors epsilon-aminocaproic acid, Suramin and tranexamic acid all have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972). It has also been reported that the drug pentosan-poly-sulfoester has an anticomplementary activity on human serum both in vitro and in vivo, as judged by the reduction in total hemolytic complement activity; Pathologie Biologie, 25, 33–36 (1977).

SUMMARY OF THE INVENTION

This invention is concerned with tetranaphthalene sulfonic acid ureylene salts, having complement inhibiting activity, which are new compounds of formula I:

FORMULA I

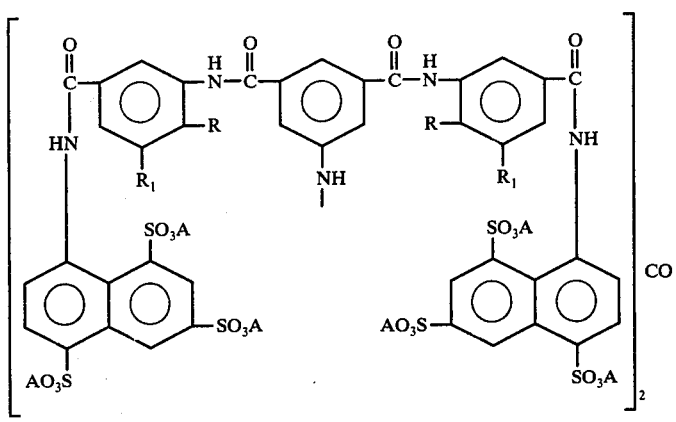

wherein R is selected from the group consisting of hydrogen and methyl; $R_1$ is selected from the group consisting of hydrogen and carboxyl; A is a pharmaceutically acceptable salt cation.

A preferred embodiment of the instant invention consists of those compounds wherein $R_1$ is hydrogen; and R and A are as previously defined.

A second preferred embodiment of the instant invention consists of those compounds wherein $R_1$ is carboxyl; and R and A are as previously defined.

A most preferred embodiment of the second preferred embodiment consists of those compounds wherein A is sodium.

This invention is also concerned with compounds of formula II:

FORMULA II

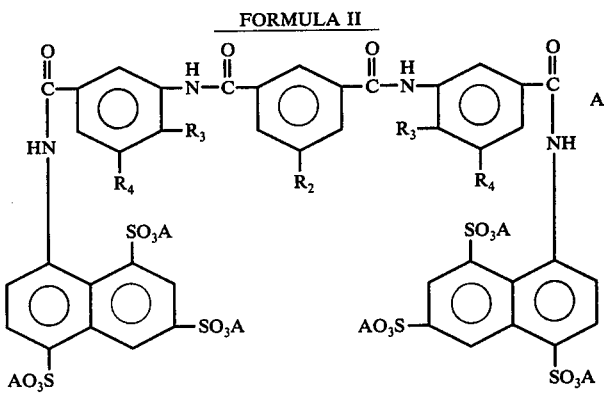

wherein $R_2$ is selected from the group consisting of nitro and amino; $R_3$ is selected from the group consisting of hydrogen and methyl; $R_4$ is selected from the group consisting of hydrogen and carboxyl; and A is selected from the group consisting of alkali metal.

A preferred embodiment of the instant invention consists of those compounds wherein $R_4$ is hydrogen; and $R_2$, $R_3$ and A are as previously defined.

A second preferred embodiment of the instant invention consists of those compounds wherein $R_4$ is carboxyl; and $R_2$, $R_3$ and A are as previously defined.

The compounds described immediately above are useful as intermediates for the preparation of the complement inhibiting ureide compounds previously described. Certain of the instant intermediates possess complement inhibiting activity.

DESCRIPTION OF THE INVENTION

The compounds of the present invention may be prepared by the following method outlined in Flow Chart A.

FLOW CHART A

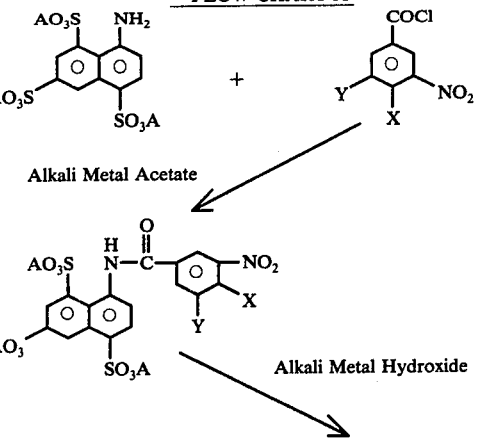

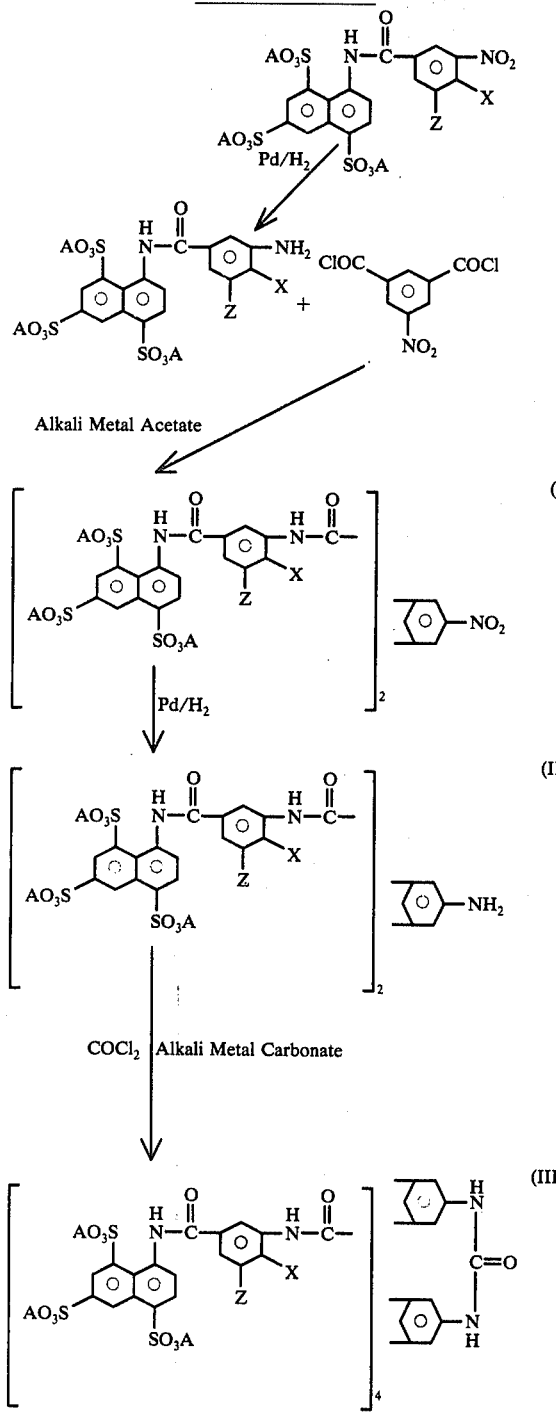

FLOW CHART A (continued)

wherein X is selected from the group consisting of hydrogen and methyl; Y is selected from the group consisting of hydrogen and carbomethoxy; Z is selected from the group consisting of hydrogen and carboxyl; and A is selected from the group consisting of alkali metal.

The novel intermediate nitro (I) and amino (II) compounds of the invention are prepared by reacting 8-amino-1,3,5-naphthalenetrisulfonic acid trialkali metal salt with the appropriate substituted nitro, substituted methyl or carbomethoxy aryl carbonyl chloride in basic aqueous medium for about 4 to about 5 hours. After acidification and neutralization, the solution is diluted with ethanol to provide the corresponding substituted nitro, substituted methyl or carbomethoxy aryl carbonylimino substituted trialkali metal salt of 1,3,5-naphthalenetrisulfonic acid. The methyl ester compound is converted to the carboxylic acid by treatment with alkali metal hydroxide, acidification with dilute hydrochloric acid and precipitation from water:ethanol (1:10). Hydrogenation of the preceding nitro trialkali metal salt using 10% palladium-carbon catalyst, filtration, concentration and treatment with absolute ethanol provides the corresponding substituted amino, substituted methyl or carboxylic acid aryl carbonylimino substituted trialkali metal salt of 1,3,5-naphthalenetrisulfonic acid. The amino trialkali metal salt dissolved in aqueous medium and neutralized to pH 7.2 is reacted with 5-nitro-isophthaloyl chloride for about 2 to about 3 hours, in the presence of alkali metal acetate. Filtration and evaporation of the filtrate provides a residue which is dissolved in water, acidified to pH 2.0–2.5 and diluted with absolute ethanol to precipitate the nitro-phenylenebiscarbonylimino substituted phenylenecarbonylimino di-1,3,5-naphthalenetrisulfonic acid hexaalkali metal salt (I). Hydrogenation of (I) using 10% palladium-carbon catalyst in water, filtration and evaporation of the filtrate produces a residue which is dissolved in water and precipitated with absolute ethanol, (water:ethanol 1:10) to yield the amino-phenylenebiscarbonylimino substituted phenylenecarbonylimino di-1,3,5-naphthalenetrisulfonic acid hexaalkali salt (II). Phosgenation of (II) in aqueous medium with alkali metal carbonate and adjustment to pH 7.0–7.2, filtration and evaporation provides a residue. The residue is dissolved in water and reprecipitated from water:ethanol (1:3) to provide the carbonyldiimino symmetrical phenenylbiscarbonylimino substituted phenylenecarbonylimino tetra-1,3,5-naphthalenetrisulfonic acid dodecaalkali metal salt (III).

The compounds of the present invention may be administered internally, e.g., orally, intra-articularly or parenterally, e.g., intra-articular, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore as well as the sodium salt, those of the alkali metals, such as potassium and lithium; of ammonia; and of the alkaline earth metals, such as calcium or magnesium, may be employed. It will be apparent, therefore, that these salts embrace, in general derivatives of salt-forming cations.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test, Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test, Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test, Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests, code 026, 035, 036, Cap 50, % inhibition and Forssman shock. Table I shows that the compounds of the invention possess highly significant in vitro and in vivo, complement inhibiting activity in warm-blooded animals.

Table II indicates the complement inhibiting activity of an intermediate compound of the invention.

TABLE I

Biological Activities

| Compound | Cl 026* Wells | C-Late 035* Wells | Shunt Inhibition 036* Wells | Cap 50* | In Vivo Activity (Guinea Pig) % Inhibition Intraperitoneal Time (Minutes) | | |
|---|---|---|---|---|---|---|---|
| | | | | | 30 | 60 | 120 |
| 8,8′,8″,8‴-{Ureylenebis{s-phenenylbis-[carbonylimino(4-methyl-3,1-phenylene)-carbonylimino)]}tetra-1,3,5-naphthalene-trisulfonic acid dodecasodium salt | +6** | +3 | +4 | 192 | −62 | −84 | −95 |
| 3,3′,3″,3‴-{Ureylenebis[s-phenenylbis-(carbonylimino)]}tetrakis[5-(4,6,8-tri-sulfo-1-naphthyl)carbamoyl]benzoic acid dodecasodium salt | +7 | +2 | +5 | 72 | −90 | −94 | −89 |

*Code designation for tests employed as referred herein.
**Activity in wells a serial dilution assay. Higher well number indicates higher activity. The serial dilutions are two-fold.

TABLE

Biological Activities (Intermediate)

| Compound | Cl 026* Wells | C-Late 035* Wells | Shunt Inhibition 036* Wells | Cap 50* | In Vivo Activity (Guinea Pig) % Inhibition Intraperitoneal Time (Minutes) | | |
|---|---|---|---|---|---|---|---|
| | | | | | 30 | 60 | 120 |
| 3,3′-[5-Amino-m-phenylenebis(carbonyl-imino)]bis{5-[4,6,8-trisulfo-1-naphthyl)carbamoyl]}benzoic acid hexasodium salt | +4** | +2 | +2 | 144 | −40 | −61 | −61 |

*Code designation for tests employed as referred herein.
**Activity in wells a serial dilution assay. Higher well number indicates higher activity. The serial dilutions are two-fold.

DETAILED DESCRIPTION OF THE INVENTION

EXAMPLE 1

8,8′-{(5-Nitro-1,3-phenylene)bis[carbonylimino(4-methyl-3,1-phenylene)carbonylimino]}di-1,3,5-naphthalenetrisulfonic acid hexasodium salt To a warm solution of 106.4 g of (80.5%) 8-amino-1,3,5-naphthalenetrisulfonic acid in 100 ml of water and 45.0 ml of 5N sodium hydroxide is slowly added 500 ml of absolute ethanol with vigorous stirring for 30 minutes. The mixture iw cooled to room temperature and filtered. The precipitate is washed with 80% aqueous ethanol, ethanol and ether and is dried in vacuo at 110° C. for 16 hours to give 103.7 g of 8-amino-1,3,5-naphthalenetrisulfonic acid trisodium salt.

A mixture of 25.0 g of 4-methyl-3-nitrobenzoic acid and 50 ml of thionyl chloride is refluxed for 3½ hours in a 110° C. oil bath. The resulting solution is evaporated in vacuo to an oil. The oil is distilled at a pressure of 0.5 mm of mercury and an oil bath temperature of 145°-160° C. The fraction, bp 108°-113° C., is collected to give 24.3 g of 3-nitro-p-toluoyl chloride.

To a stirred solution of 22.5 g of 8-amino-1,3,5-naphthalenetrisulfonic acid trisodium salt in 160 ml of water is added 11.0 g of the preceding product with a small amount of ether. Stirring is continued, and after one hour 1.0 g of sodium acetate trihydrate and 1.0 g of 3-nitro-p-toluoyl chloride are added. The mixture is stirred an additional 3 hours and the above addition of sodium acetate and 3-nitro-p-toluoyl chloride is repeated. The mixture is stirred an additional hour, acidified to Congo Red indicator paper with hydrochloric acid and filtered. The filtrate is neutralized with sodium hydroxide, concentrated, dissolved in 50 ml of water and added to 1 liter of ethanol with stirring for 16 hours. The solid is filtered and forms a gel on washing with ethanol. The gel is dissovled in water and evaporated. The residue is dissolved in 35 ml of hot water and 320 ml of absolute ethanol is added with stirring. The mixture solidifies and water is added to allow filtration. The solid is washed with ether and dried in vacuo. The filtrate is treated by stirring with one liter of ethanol, the separated solid is collected, washed with ether, and dried to yield a combined total of 23.9 g of 8-(3-nitro-p-toluamido)-1,3,5-naphthalenetrisulfonic acid trisodium salt.

A 22.0 g portion of the preceding product, 200 ml of water and 2.5 g of 10% palladium-on-carbon catalyst is hydrogneated in a Parr shaker until no more hydrogen is absorbed. The resulting mixture is filtered through diatomaceous earth, the residue is washed with water, and the filtrate is evaporated, the residue is dissolved in 50 ml of water and added to 900 ml of absolute ethanol. The mixture is warmed on a steam bath and then is stirred at room temperature for 3 hours. The mixture is filtered and the solid is washed with ethanol, then ether and dried in vacuo to give 16.89 g of 8-(3-amino-p-toluamido)-1,3,5-naphthalenetrisulfonic acid trisodium salt.

A mixture of 60.0 g of 5-nitroisophthalic acid, 300 ml of thionyl chloride and one ml of dimethylformamide is stirred at room temperature for 30 minutes, then is refluxed for one hour. The resulting clear solution is allowed to stand 24 hours, then is evaporated to a small volume in vacuo. The evaporation step is repeated with toluene and the resulting liquid is diluted with 250 ml of hexane. The mixture is stirred and cooled until the resulting oil is solidified. The product is ground to a powder and is recrystallized twice from carbon tetrachloride to give 47.4 g of 5-nitroisophthaloyl chloride.

A stirred solution of 10.6 g of 8-(3-amino-p-toluamido)-1,3,5-naphthalenetrisulfonic acid trisodium salt in 60 ml of water is neutralized to pH 7.2, then 2.84 g of sodium acetate trihydrate is added followed by 2.48 g of powdered 5-nitroisophthaloyl chloride with vigorous stirring. Stirring is continued for 2 hours, the reaction mixture is filtered, and the filtrate evaporated in vacuo. The residue is dissolved in 50 ml of hot water and acidified to pH 2.5, then 70 ml of absolute ethanol is added with vigorous stirring to form a precipitate. The mixture is heated until solution results and then allowed to cool with stirring. The reprecipitated product is collected, washed with 70% aqueous ethanol, ethanol and ether, then is dried to yield 10.6 g of the product of the Example.

EXAMPLE 2

8,8'-{5-Amino-1,3-phenylenebis{{[carbonylimino(4-methyl-3,1-phenylene)]carbonyl}imino}}di-1,3,5-naphthalenetrisulfonic acid hexasodium salt A mixture of 1.98 g of the product of Example 1, 60 ml of water and 500 mg of 10% palladium-on-carbon catalyst is hydrogenated in a Parr shaker. The resulting mixture is filtered, and the filtrate is evaporated. The residue is dissolved in 12 ml of hot water and 125 ml of absolute ethanol is added. The precipitate is collected, washed with ethanol and ether and dried to yield 1.73 g of the product of the Example.

EXAMPLE 3

8,8',8'',8'''-{Ureylenebis{s-phenenylbis[carbonylimino(4-methyl-3,1-phenylene)carbonylimino]}}·tetra-1,3,5-naphthalenetrisulfonic acid dodecasodium salt Phosgene gas is bubbled into a mixture of 1.73 g of the product of Example 2, 290 mg of sodium carbonate and 20 ml of water until acidic to Congo Red indicator paper. The mixture is adjusted to pH 7.0 and filtered. The filtrate is evaporated. The residue is dissolved in 10 ml of hot water, then ethanol is added producing a gum. The supernatant is decanted, the gum is triturated with ethanol and solidifies. The solid is collected by filtration, washed with ethanol and ether and dried. The material is dissolved in 15 ml of water, reprecipitated with 50 ml of ethanol, stirred for 1 hour, filtered, washed as above and dried to yield 1.5 g of the product of the Example.

EXAMPLE 4

3,3'-[5-Nitro-m-phenylenebis(carbonylimino)]bis-{5-[(4,6,8-trisulfo-1-naphthyl)carbamoyl]}benzoic acid hexasodium salt A 35.0 g portion of 5-nitroisophthaloyl chloride is added to 600 ml of methanol with stirring producing a precipitate. The mixture is heated to solution then is chilled, filtered and dried to yield 31.75 g of dimethyl 5-nitroisophthalate.

A mixture of 7.46 g of potassium hydroxide in 87.5 ml of methanol is added to a stirred solution of 31.75 g of the preceding product in 331.0 ml of acetone. A solid is precipitated and stirring is continued for 16 hours. The solid (A) is filtered off, washed with ether and set aside. The filtrate is evaporated, the residue is extracted with 125 ml of warm water and is filtered. The filtrate is acidified with dilute hydrochloric acid to produce a precipitate which is collected and dried to yield 3.4 g of product. The solid (A) above is extracted with 250 ml of warm water and is filtered. The filtrate is filtered again at room temperature, acidified with dilute hydrochloric acid and cooled. The precipitate is collected and dried to give 18.25 g of additional product identified as 5-nitro-isophthalic acid, 3-methyl ester.

A mixture of 18.38 g of the product above, 60 ml of thionyl chloride and 0.37 ml of dimethylformamide is heated at 60° C. for 2.5 hours. The solution is evaporated, then is treated with toluene, and again is evaporated. The residue is slurried in hot diethyl ether and the ether volume is reduced by evaporation. The mixture is chilled and filtered. The precipitate is washed with cold ether and is dried. The material is extracted with 500 ml of boiling hexane by decantation. The hexane is cooled and filtered to yield 14.1 g of 3-carbomethoxy-5-nitrobenzoyl chloride.

To a solution of 14.0 g of 8-amino-1,3,5-naphthalenetrisulfonic acid trisodium salt and 8.96 g of sodium acetate trihydrate in 150 ml of water is added with stirring 8.0 g of 3-carbomethoxy-5-nitrobenzoyl chloride. Stirring is continued for 2 hours then 18.0 ml of diethyl ether is added and stirring is continued for one additional hour. An additional 1.12 g of sodium acetate is added along with 1.0 g of 3-carbomethoxy-5-nitrobenzoyl chloride with continued stirring for one hour. The mixture is filtered and the filtrate is concentrated. The residue is dissolved in 100 ml of hot water, 100 ml of absolute ethanol is added with formation on standing of a precipitate. The material is filtered, washed with 80% aqueous ethanol, ethanol and ether and dried to yield 17.35 g of 5-nitro-N-4,6,8-trisulfo-1-naphthylisophthalamic acid methyl ester trisodium salt.

A 12.0 g portion of the above product in 183.0 ml of 0.1N sodium hydroxide is stirred for 3 hours. The solution is acidified to pH 2.0 with dilute hydrochloric acid then is evaporated. The residue is dissolved in 35 ml of hot water and 350 ml of absolute ethanol is added. The precipitated product is filtered, washed with ethanol and ether and dried to yield 11.0 g of 5-nitro-N-4,6,8-trisulfo-1-naphthylisophthalamic acid trisodium salt A mixture of 11.0 g of the preceding compound and 2.0 g of 10% palladium-on-carbon catalyst in 100 ml of water is hydrogenated in a Parr shaker until no additional hydrogen is absorbed. The resulting mixture is filtered through diatomaceous earth, the filtrate is evaporated, the residue is dissolved in 35 ml of hot water, then is diluted with 350 ml of aboslute ethanol to yield a precipitate. The product is collected, washed with ethanol and ether, and dried to give 8.6 of 5-amino-N-4,6,8-trisulfo-1-naphthylisophthalamic acid trisodium salt.

A stirred solution of 8.6 g of the above compound in 50 ml of water is neutralized to pH 7.2, then 2.2 g of sodium acetate trihydrate is added followed by 1.92 g of powdered 5-nitroisophthaloyl chloride with vigorous stirring. Stirring is continued for an additional 3 hours then the reaction mixture is filtered and evaporated in vacuo. The residue is dissolved in 50 ml of water and acidified to pH 2.0 A solid is precipitated by the slow addition of 120 ml of absolute ethanol with stirring for ½ hour. The solid is filtered, washed with 80% aqueous ethanol, ethanol and ether and dried in vacuo to yield 10.1 g of the product of the Example.

EXAMPLE 5

3,3'-[5-Amino-m-phenylenebis(carbonylimino)]bis{5-[4,6,8-trisulfo-1-naphthyl)carbamoyl]}benzoic acid hexasodium salt A mixture of 9.1 g of the product of Example 4, 1.3 g of 10% palladium-on-carbon catalyst and 150 ml of water is hydrogenated in a Parr shaker until no additional hydrogen is absorbed. The resulting mixture is filtered through a diatomaceous earth. The filtrate is evaporated, the residue is dissolved in 50 ml of hot water and 500 ml of absolute ethanol is added with stirring. Stirring is continued for 1 hour. The product is filtered, washed with ethanol and ether and dried to yield 7.3 g of the product of the Example.

EXAMPLE 6

3,3',3'',3'''-{Ureylenebis[s-phenenylbis(carbonylimino)]}-tetrakis[5-(4,6,8-trisulfo-1-naphthyl)carbamoyl]benzoic acid dodecasodium salt Phosgene gas is bubbled into a solution of 6.6 g of the product of Example 5 and 1.56 g of sodium carbonate in 60.0 ml of water until acidic to Congo Red indicator paper. The mixture is adjusted to pH 7.2 with sodium carbonate, treated with activated charcoal and filtered. The filtrate is concentrated and the residue is dissolved in 40.0 ml of hot water then ethanol is added to a volume of 140 ml to form a gum. The supernatant is decanted and the gum is triturated with ethanol to yield a solid. The solid is filtered, washed with ethanol and ether and dried. The material is dissovled in 40.0 ml of hot water and is added to 140 ml of ethanol to again give a gum. The gum is collected, dissolved in water and evaporated. The residue is dissolved in 50 ml of water, adjusted to pH 2.0 with hydrochloric acid and treated with 140 ml of ethanol. The supernatant is decanted and the residue is triturated with ethanol, filtered, washed with ethanol and ether and dried to yield 5.1 g of the product of the Example as a tan solid.

EXAMPLE 7

| Preparation of Compressed Tablet | |
|---|---|
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 8

| Preparation of Compressed Tablet - Sustained Action | |
|---|---|
| Ingredient | mg/Tablet |
| Active Compound as Aluminum Lake*, Micronized | 0.5–500(as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 9

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 10

| Preparation of Oral Liquid (Syrup) | |
|---|---|
| Ingredient | % W/V |
| Active Compound | 0.05–5 |
| Liquid Sugar | 75.0 |

| -continued | |
|---|---|
| Preparation of Oral Liquid (Syrup) | |
| Ingredient | % W/V |
| Methyl Paraben USP | 0.18 |
| Propyl Paraben USP | 0.02 |
| Flavoring Agent | qs |
| Purified Water qs ad | 100.0 |

EXAMPLE 11

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 12

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 13

| Preparation of Injectable Solution | |
|---|---|
| Ingredient | % W/V |
| Active Compound | 0.05–5 |
| Benzyl Alcohol N.F. | 0.9 |
| Water for Injection | 100.0 |

EXAMPLE 14

| Preparation of Injectable Oil | |
|---|---|
| Ingredient | % W/V |
| Active Compound | 0.05–5 |
| Benzyl Alcohol | 1.5 |
| Sesame Oil qs ad | 100.0 |

EXAMPLE 15

| Preparation of Intra-Articular Product | |
|---|---|
| Ingredient | Amount |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 16

| Preparation of Injectable Depo Suspension | |
|---|---|
| Ingredient | % W/V |
| Active Compound | 0.05–5 |

-continued

Preparation of Injectable Depo Suspension

| Ingredient | % W/V |
|---|---|
| | (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

We claim:

1. A compound of the formula:

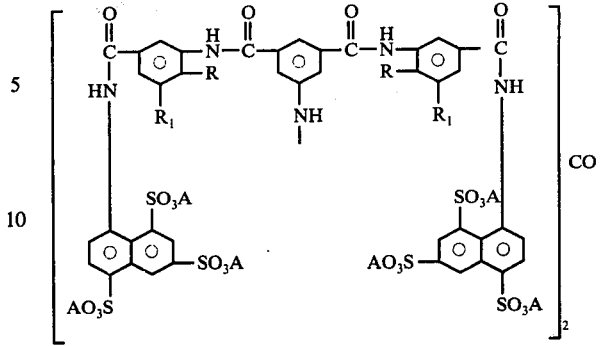

wherein R is selected from the group consisting of hydrogen and methyl; $R_1$ is selected from the group consisting of hydrogen and carboxyl; A is a pharmaceutically acceptable salt cation.

2. A compound according to claim 1, wherein $R_1$ is hydrogen; and R and A are as previously defined.

3. A compound according to claim 1, wherein $R_1$ is carboxyl; and R and A are as previously defined.

4. A compound according to claim 3, wherein A is sodium.

5. The compound according to claim 1, 8,8',8",8"'-{ureylenebis{s-phenenylbis[carbonylimino(4-methyl-3,1-phenylene)carbonylimino]}}tetra-1,3,5-naphthalenetrisulfonic acid dodecasodium salt.

6. The compound according to claim 1, 3,3',3",3"'-{ureylenebis[s-phenenylbis(carbonylimino)]}tetrakis [5-(4,6,8-trisulfo-1-naphthyl)carbamoyl]benzoic acid dodecasodium salt.

* * * * *